US012700088B2

(12) United States Patent
Lin et al.

(10) Patent No.: US 12,700,088 B2
(45) Date of Patent: Aug. 4, 2026

(54) METHODS AND SYSTEMS FOR IDENTIFICATION OF TRABECULAR MESHWORK OR OTHER INTRAOCCULAR ANATOMICAL STRUCTURES AND TISSUE TYPES

(71) Applicant: The Regents of the University of California, Oakland, CA (US)

(72) Inventors: Ken Y. Lin, Irvine, CA (US); Pierre Baldi, Irvine, CA (US); Gregor Urban, Mountain View, CA (US)

(73) Assignee: The Regents of the University of California, Oakland, CA (US)

( * ) Notice: Subject to any disclaimer, the term of this patent is extended or adjusted under 35 U.S.C. 154(b) by 306 days.

(21) Appl. No.: 18/386,576

(22) Filed: Nov. 2, 2023

(65) Prior Publication Data

US 2024/0153076 A1 May 9, 2024

Related U.S. Application Data

(60) Provisional application No. 63/422,859, filed on Nov. 4, 2022.

(51) Int. Cl.
| | |
|---|---|
| *G06T 7/00* | (2017.01) |
| *G16H 10/60* | (2018.01) |
| *G16H 30/40* | (2018.01) |
| *G16H 40/67* | (2018.01) |

(52) U.S. Cl.
CPC ........... *G06T 7/0012* (2013.01); *G16H 10/60* (2018.01); *G16H 30/40* (2018.01); *G16H 40/67* (2018.01); *G06T 2207/10021* (2013.01); *G06T 2207/20084* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 2019/0357768 A1 | 11/2019 | Shareef | |
| 2021/0007795 A1 | 1/2021 | Johnson | |
| 2021/0298945 A1 | 9/2021 | Juhasz et al. | |
| 2022/0180518 A1 | 6/2022 | Agus et al. | |
| 2022/0346884 A1 * | 11/2022 | Leiderman | G06V 40/18 |
| 2023/0301727 A1 * | 9/2023 | Leiderman | G16H 40/63 |

FOREIGN PATENT DOCUMENTS

WO WO2019/012551 A1 1/2019

OTHER PUBLICATIONS

Ken Y. Lin et al., "Accurate Identification of the Trabecular Meshwork under Gonioscopic View in Real Time Using Deep Learning," American Academy of Ophthalmology, 2021, pp. 402-412.
Sean Ianchulev, "Robot-Assisted Glaucoma Surgery, Reaching New Levels of Precision in Surgical Glaucoma Care with a First-In-Class Robotic System," Glaucoma Today, Nov./Dec. 2021, pp. 31-32.

* cited by examiner

*Primary Examiner* — Dov Popovici
(74) *Attorney, Agent, or Firm* — Robert D. Buyan; Stout, Uxa & Buyan, LLP

(57) ABSTRACT
Devices, systems, kits, software and methods for using deep learning for enhanced identification of anatomical structures or tissue types during eye surgery.

20 Claims, 6 Drawing Sheets
(3 of 6 Drawing Sheet(s) Filed in Color)

*Cross-sectional View of CNN Targets*

*CNN Targets*

*Expert TM Line Annotations*

METHODS AND SYSTEMS FOR IDENTIFICATION OF TRABECULAR MESHWORK OR OTHER INTRAOCCULAR ANATOMICAL STRUCTURES AND TISSUE TYPES

RELATED APPLICATION

This patent application claims priority to U.S. Provisional Patent Application No. 63/422,859 entitled Methods and Systems for Identification of Trabecular Meshwork or Other Intraoccular Anatomical Structures and Tissue Types, filed Nov. 4, 2022, the entire disclosure of which is expressly incorporated herein by reference.

FIELD

This patent application pertains generally to the fields of biomedical engineering, medicine, surgery and information technology, and more particularly to devices, methods, systems, kits and software useable for enhanced tissue identification during eye surgery.

BACKGROUND

Pursuant to 37 CFR 1.71(e), this patent document contains material which is subject to copyright protection and the owner of this patent document reserves all copyright rights whatsoever.

Various types of eye surgery require precise identification of anatomical structures and/or tissue types within the eye. For example, in certain minimally invasive or micro-invasive glaucoma surgeries (MIGS), such as laser trabeculoplasty, goniotomy, trabeculectomy, trabeculotomy or stent implantation, it is necessary for the surgeon to view and identify small anatomical structures and tissue types within the iridocorneal angle of the eye. One such anatomical structure that can be difficult to identify is a narrow three-dimensional band of fenestrated tissue known as trabecular meshwork (TM).

In a healthy eye, a fluid known as aqueous humor is produced within the eye, accumulates in the anterior chamber of the eye, and then drains outwardly from the anterior chamber, through fenestrations in the trabecular meshwork, and into an annular Canal of Schlemm. Aqueous humor that enters the Canal of Schlemm then passes through a network of collector channels and is carried away through the venous circulation. In some types of glaucoma, outflow of aqueous humor from the eye is impaired, thereby resulting in increased intraoccular pressure. In some glaucoma treatment surgeries, such as MIGS procedures, openings or passages are formed in the trabecular meshwork to increase the outflow of aqueous humor, thereby lowering the elevated intraoccular pressure. Successful performance of such surgical procedures requires accurate identification of the trabecular meshwork. Misidentification of the trabecular meshwork can adversely affect surgical outcomes and, in some cases, can result in undesirable post-surgical complications.

Accurately identifying the trabecular meshwork can be challenging, especially for novice surgeons. This is due, at least in part, to differences in trabecular meshwork pigmentation and individual variability of the iridocorneal angle anatomy.

Deep Learning is a type of machine learning which uses artificial neural networks in which multiple layers of processing are used to extract progressively higher level features from data. As described below, Applicant has devised new systems and methods which use deep learning to accurately identify the trabecular meshwork tissue or other anatomical structures or tissue types within the eye.

SUMMARY

Described herein is a system for identifying an anatomical structure or tissue type within an eye of a subject, said system comprising: a viewing device for viewing an area within the eye which includes the anatomical structure or tissue type; a camera or imaging device; an image processor; and a display device; wherein the camera or imaging device acquires an image of the area viewed by the viewing device; wherein the image processor uses deep learning to identify the anatomical structure or tissue type on said image; and wherein the display device displays an enhanced image on which the anatomical structure or tissue type is marked.

In some embodiments of an above-summarized system, the viewing device may be selected from: goniolens, gonioprism, gonioscope, retnascope, ophthalmoscope and surgical microscope.

In some embodiments of an above-summarized system, the camera or imaging device may comprise a still camera or a video camera.

In some embodiments of an above-summarized system, the image processor may comprise a computer or processor.

In some embodiments of an above-summarized system, the display device is selected from: a video screen, monocular or binocular eyepiece, virtual reality headset/goggles/glasses.

In some embodiments of an above-summarized system, the anatomical structure or tissue type is may be selected from: trabecular meshwork, macula, retinal pigment epithelium, optic nerve head, epiretinal membranes.

In some embodiments of an above-summarized system, the viewing device views the iridocorneal angle and the anatomical structure or tissue type is trabecular meshwork.

In some embodiments of an above-summarized system, the anatomical structure or tissue type may be marked on the enhanced image by a type of marking selected from: delineation, accentuation, darkening, coloring, annotation or indication with an arrow or pointer.

In some embodiments of an above-summarized system, the image processor may be programmed to apply Neural Encoder-Decoder Convolutional Neural Networks (CNNs) (U-nets) trained to identify the anatomical structure or tissue.

In some embodiments of an above-summarized system, the system may be equipped to transmit the enhanced image to a local or remote secondary location. In some such embodiments, the secondary location may be selected from: a local or cloud-based data storage medium, hard drive, intraoperative recording device, remote computer, remote display, telemedicine terminal, medical records database or surgical robot.

In some embodiments of an above-summarized system, the image processor may comprise a non-transitory data storage medium having recorded thereon a deep-learning generative model that outputs said enhanced image on which the anatomical structure or tissue type is marked. In some such embodiments, the deep-learning generative model may comprise a CNN configured as an encoder and decoder network that is able to generate predictions for every pixel in said image. In some such embodiments, the CNN may be trained using video image frames that are down-sampled to a size of 512×288 pixels. In some such embodiments, the CNN may be trained by a method which uses multitask learning, whereby the CNN is trained to predict not only the target anatomical structure or tissue type but also an ancillary anatomical structure or tissue type.

In some embodiments of an above-summarized system, the target anatomical structure or tissue type is trabecular meshwork and the ancillary anatomical structure or tissue type is iris border.

In some embodiments of an above-summarized system wherein the deep-learning generative model comprises a CNN, the CNN may be trained using data augmentation. In some such embodiments, the data augmentation may comprise at least one of: horizontal mirroring; random translations of images up to ±10% of the image height; rotations up to ±25 degrees; shearing up to ±20 degrees; zooming up to ±10% of the image height; and small random changes to the color balance of any red/green/blue channels of an image. In some such embodiments, any pixels with missing values after augmentation may be populated by replicating the closest pixel values of the image.

In some embodiments of an above-summarized system wherein the deep-learning generative model comprises a CNN, the cross-validation was applied during training of the CNNs. In some such embodiments, the cross-validation may comprise a per-patient stratified ten-fold cross-validation.

Further described herein is a method for using any of the systems summarized above, such method comprising the steps of: positioning the viewing device to view said area within the eye which includes the anatomical structure or tissue type; causing the camera or imaging device to acquire an image of said area which includes the anatomical structure or tissue type; causing the image processor to process said image using deep learning to identify the anatomical structure or tissue type; and causing the display device to display said enhanced image of said area on which the anatomical structure or tissue type is marked.

In some embodiments of the above-summarized method, the method may be performed intraoperatively.

In some embodiments of the above-summarized method, the anatomical structure or tissue type is trabecular meshwork and the method is performed intraoperatively during surgery to treat glaucoma or to lower intraoccular pressure.

In some such methods, the method may be performed intraoperatively during minimally invasive or micro-invasive glaucoma surgery (MIGS). In some such methods, the method may be performed intraoperatively during a glaucoma surgery selected from: laser trabeculoplasty, goniotomy, trabeculectomy, trabeculotomy or stent implantation.

Further described herein is a kit for modification of a gonioscopic device, surgical microscope system, or other apparatus which generates images of areas within an eye, said kit comprising: a replacement or add on image processor programmed to process the image using deep learning to identify a particular intraoccular anatomical structure or tissue type of interest in accordance with the present disclosure.

Still further described herein is a software package or software update for modifying or updating an existing image processor of a gonioscopic device, surgical microscope system, or other apparatus which generates images of areas within an eye, said software package or software update comprising: a non-transitory data storage medium having recorded thereon a deep-learning generative model that causes the existing image processor to output an enhanced image on which a particular intraoccular anatomical structure or tissue type of interest is marked.

Still further aspects and details of the present disclosure will be understood upon reading of the detailed description and examples set forth herebelow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures are included in this patent application and referenced in the following Detailed Description. These figures are intended only to illustrate certain aspects or embodiments of the present disclosure and do not limit the scope of the present disclosure in any way.

DETAILED DESCRIPTION

The following written description and the accompanying drawings describe some, but not necessarily all, examples or embodiments of the disclosed systems and methods. The described examples or embodiments are to be considered as illustrative but not restrictive, and shall not limit the scope of any patent claims which may be based on this disclosure in any way.

Figure 1:
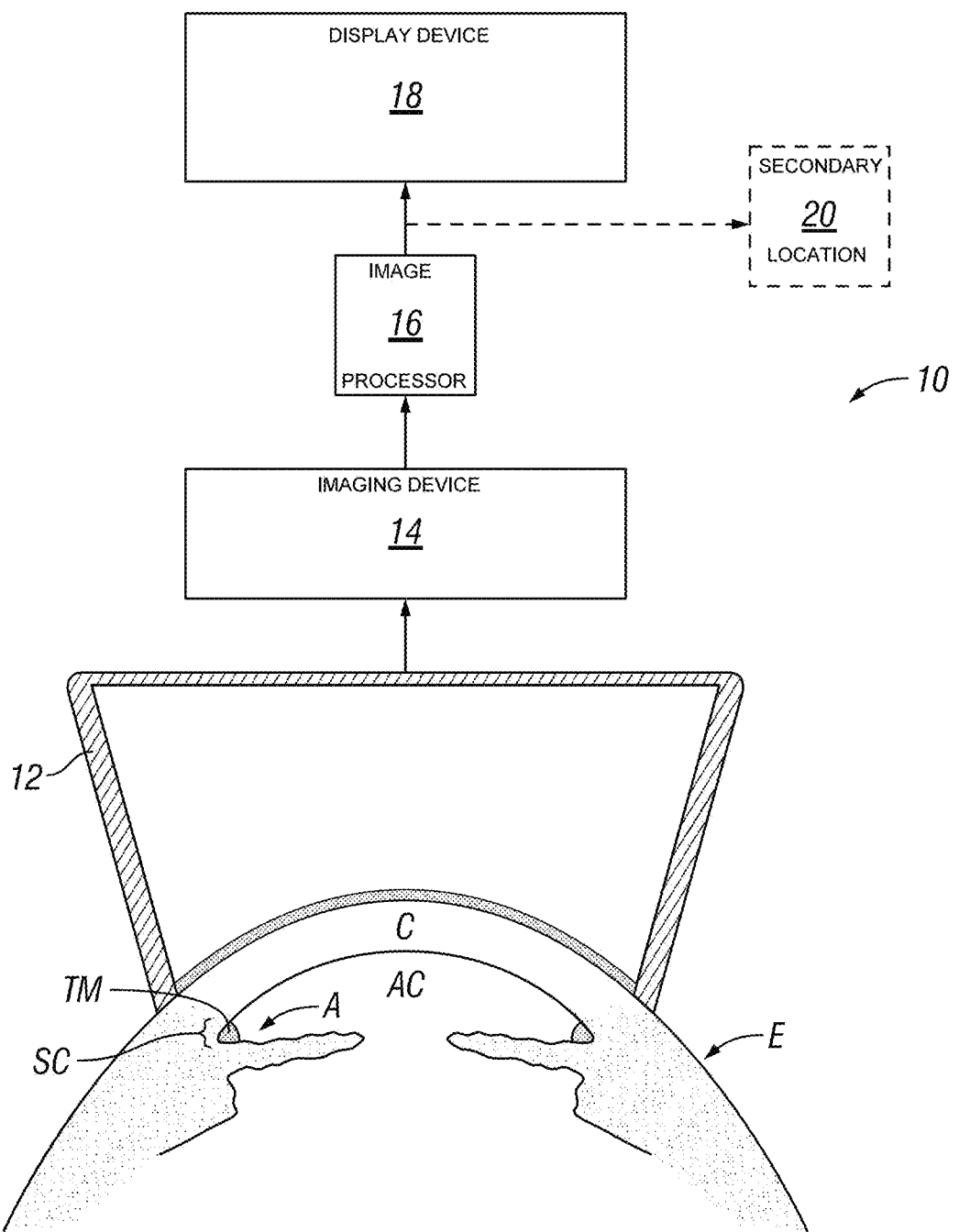
FIG. 1 is a schematic diagram showing one embodiment of a trabecular meshwork identification system in accordance with the present disclosure.

FIG. 1 is a component diagram which shows one example of a system 10 for identification of an intraoccular anatomical structure or tissue type within an eye E of a subject. This system 10 comprises: a viewing device 12 for viewing the tissue or anatomical structure (e.g., a goniolens, gonioprism, gonioscope, retnascope, ophthalmoscope, surgical microscope, etc.); a camera or imaging device 14 (e.g., a video camera); an image processor 16 (e.g., a computer or processor); and, a display device 18 (e.g., a video screen, and/or monocular or binocular eyepiece, virtual reality headset/ goggles/glasses, etc.).

In the particular example of FIG. 1, the viewing device 12 comprises a gonioscopic device that is positioned on the cornea C of the eye E for viewing the iridocorneal angle A and the image processor 16 is programmed to identify the trabecular meshwork TM, which overlies the Canal of Schlemm SC, as the anatomical structure or tissue type of interest. It is to be understood, however, that this is just one non-limiting example. Indeed, other types of intraoccular viewing devices 12 can be used (e.g., devices for viewing the retina) and the image processor 16 can be programmed to identify intraoccular anatomical structures or tissue types other than trabecular meshwork TM (e.g., macula, retinal pigment epithelium, optic nerve head, epiretinal membranes, etc.).

Optionally, the system 10 can be equipped to transmit the enhanced image to a local or remote secondary location 20, such as a local or cloud-based data storage medium, hard drive, intraoperative recording device, remote computer, remote display, telemedicine terminal, medical records database, surgical robot, etc.

In typical operation of the system 10, the camera or imaging device 14 acquires an image of an area within the eye that includes the intraoccular tissue or anatomical structure of interest. The image processor 16 then processes the acquired image using deep learning to identify a particular anatomical structure(s) or tissue type(s) of interest. The display device 18 then displays an enhanced image on which the particular anatomical structure(s) or tissue type(s) of interest is/are marked (e.g., delineated, accentuated, darkened, colored, annotated, indicated with an arrow or pointer, or otherwise identified).

The image processor 16 of the system 10 shown in FIG. 1 may be programmed to apply Neural Encoder-Decoder CNNs (U-nets) trained to identify the anatomical structure or tissue type of interest. Training of the CNNs can be accomplished in several ways. One approach is to use a pixel-wise segmentation model, such as a U-net, and predict each pixel that is close to the TM as "1" and everything else as "0." Another approach is to predicting a line, curve or other marking that marks the center of the anatomical structure or tissue type of interest directly, either by predicting polynomial factors, or segments of a spline graph. Alternatively, a combination of both approaches can be used, wherein the model predicts, for each pixel in the image, what this pixel's distance is to the center of the human annotation of a center of the anatomical structure or tissue type of interest, as well the direction toward that anatomical structure or tissue type, encoded as positive or negative values. The distance targets may then be capped to some suitable range. For example, in this system, the anatomical structure or tissue type of interest was trabecular meshwork TM and the distance targets were capped at ±30 pixels (which amounted to ±10% of the re-scaled image's height) and then normalized to the range of −1 to 1 to facilitate training of the CNNs.

FIGS. 2 through 7 and the following paragraphs provide a detailed example of the training and use of a system 10 of the type shown in FIG. 1 for intraoperative identification of trabecular meshwork tissue in the eye of a human or other animal subject. Neural Encoder-Decoder CNNs (U-nets) were trained to predict a curve which marks the trabecular meshwork TM by using an expert-annotated data set of 378 gonioscopy images obtained from patient eyes. The model was trained and evaluated with stratified cross-validation grouped by patients to ensure uncorrelated training and testing sets, as well as on a separate test set and 3 intraoperative gonioscopic videos of ab interno trabeculotomy. Also described is a comparison of the model's performance with manual identification of trabecular meshwork TM by experienced ophthalmologists. The best CNN model tested provided predictions which had a median deviation from the human experts' annotations of 0.8% of the video frame's height (15.25 mm). This error is less than the average vertical height of the trabecular meshwork TM. Even the worst test frame prediction had an average deviation of 4% of the frame height (76.28 mm), which is still considered a successful prediction. When challenged with unseen images, the CNN model scored greater than 2 standard deviations above the mean performance of the surveyed general ophthalmologists. Therefore, based on the studies described below, it is concluded that the herein described systems and methods are useable to accurately identify trabecular meshwork and other intraoccular anatomical structures and/or tissue types.

Example: Accurate Identification of the Trabecular
Meshwork Under Gonioscopic View in Real Time
Using Deep Learning Accurate identification of iridocorneal structures on gonioscopy is difficult to master and errors can lead to grave surgical complications. This study aimed to develop and train convolutional neural networks (CNNs) to accurately identify the trabecular meshwork (TM) in gonioscopic videos in real-time for eventual clinical integrations. In this study, adult patients with open angle were identified in an academic glaucoma clinic in both Taipei, Taiwan and Irvine, California, USA. Neural Encoder-Decoder CNNs (U-nets) were trained to predict a curve marking the TM using an expert-annotated data set of 378 gonioscopy images. The model was trained and evaluated with stratified cross-validation—grouped by patients to ensure uncorrelated training and test sets, as well as on a separate test set, and three additional videos. These videos were of intraoperative gonioscopic views of ab interno trabeculectomy with the Trabectome® system (totaling 90 seconds long, approximately 30 frames per second). We also evaluated our model's performance by comparing its accuracy against ophthalmologists.

Successful development of real-time capable CNNs that are very accurate in predicting and marking the trabecular meshwork's position in video frames of eyes under gonioscopic view. Models were evaluated in comparison to human expert annotations of static images and video data. The best CNN produces test set predictions with a median deviation of only 0.8% of the video frame's height (15.25 micron in real height) compared to human annotations. This error is less than the average vertical height of the TM. Even the worst test frame prediction of this CNN had an average deviation of 4% of the frame height (76.28 micron in real height), which can still be considered a successful prediction. When challenged with unseen images, the model scored higher than two standard deviations above the mean of general ophthalmologists.

The CNN model described herein can identify the TM in gonioscopy videos in real time with remarkable accuracy while also being able to operate in real-time, allowing it to be used in connection with a video camera in live operations. This model can have applications in surgical training, automated screenings, and intraoperative guidance. The dataset in this study is the first publicly available gonioscopy image bank which may help spur future developments in this area.

The anatomy of the iridocorneal angle involves five main structures (from anterior to posterior): Schwalbe line, Schlemm canal and TM, scleral spur, ciliary body, and the peripheral iris root. Direct visualization of the iridocorneal angle is not possible due to total internal reflection; therefore, these structures are best viewed indirectly with the use of a gonioprism. When surveyed regarding their comfort level (0-4) with four-mirror gonioscopy, ophthalmology residents and private practitioners rated it as the second most difficult (0.83 out of 4) examination skill. Furthermore, participants at the American Academy of Ophthalmology Annual Meeting's laser trabeculoplasty course consistently rated identifying the TM as one of the most challenging tasks. These findings are not particularly surprising given the wide morphological variability of the iridocorneal structures.

Variability in delineating characteristics (e.g. pigmentation) of iridocorneal structures can make identification difficult at any level of training. Unfortunately, misidentification of the iridocorneal structures intraoperatively can lead to patient harm and treatment failure. In deep sclerectomy and viscocanalostomy, there are reports of trabeculo-descemetic membrane rupture due to misidentification of Schlemm canal. In minimally invasive glaucoma surgery (MIGS), a malpositioned stent could result in treatment failure and possibly necessitating further intervention. The rate of stent malposition varies widely between studies but has been estimated to occur in 4-18% of cases. The TM is the anatomic target of laser trabeculoplasty and most types of MIGS. Improvement in the accuracy of identifying the TM would likely be helpful in reducing these complications, and deep learning appears to be an ideal candidate for building a tool to assist surgeries.

Convolutional Neural Networks (CNNs) are a class of deep learning architectures originally inspired by the pattern of neuronal connectivity in the animal visual cortex. They operate primarily by using a hierarchical arrangement of trainable banks of convolution filters, where each filter in a bank is implemented using the neuronal weight sharing approach. The weights are typically trained by stochastic gradient descent to minimize the error on the training data. With increasing architectural depth, neurons become responsive to increasingly large areas of the input image and can selectively respond to increasingly large and complex patterns.

There have been many applications of deep learning in clinical imaging, including applications to endoscopy videos. Within ophthalmology, tasks such as the identification of retinopathy of prematurity (ROP), exudates in diabetic retinopathy, glaucomatous optic neuropathy, and angle-closure glaucoma have been addressed. In these examples, CNNs were used to classify images into discrete categories (e.g. positive versus negative). Here, however, instead of simply classifying images, our study aims at creating CNNs that are capable of taking a video input and processing it in real time while accurately delineating the intended anatomic target (i.e. the trabecular meshwork). Thus, this work strives to go a few steps beyond simple image classification or segmentation.

Thus, in summary, the aims of this study were to: (1) train a real-time-capable CNN that accurately identifies and marks the trabecular meshwork in colored gonioscopic images; (2) validate the model on such images, as well as on gonioscopic surgical videos; and (3) compare the performance of the model against ophthalmologists on gonioscopy images that the model had not previously seen.

Methods

Data Set

Data was collected from 25 different patients, all of whom were e adults with open angle and no previous history of MIGS. A total of 378 gonioscopic images were taken from different clock hours of both eyes with a Volk G-3-mini non-flanged gonioprism, which includes 149 frames that were extracted from six videos of selective laser trabeculoplasty under gonioscopic view that were recorded from six different patients (every 50th frame was extracted, which reduces the amount of redundancy in the final images). The images and videos had a resolution of at least 1920 by 1080 pixels and were recorded with a Canon EOS 7D Mark II (Tokyo, Japan). Additionally, three videos of ab interno trabeculotomy with the Trabectome system with a length of 90 seconds and approximately 30 frames per second and were collected from publicly available web sources. They Were used as an additional independent test case to evaluate our deep learning model's performance, as these images were acquired by cameras and operators that were different from those that the model was trained with previously.

As summarized in Table 1, below, the demographics of this study population had an mean age of 47 years old (range of 23 to 81 years old), 59% male (n=13) and 41% female (n=9), 68% of patients had glaucoma (n=15) and 32% did not have glaucoma (n=7). The level of pigmentation of the trabecular meshwork in each image varied from 0 to 4 (lighter to darker) with 5% being grade 0 (n=21), 26% being grade 1 (n=107), 44% being grade 2 (n=180), 17% being grade 3 (n=70), and 7% being grade 4 (n=30).

TABLE 1

| Study Population Demographics All patients were adults with open angle and no history of minimally invasive glaucoma surgeries | |
|---|---|
| Category | Number of Patients |
| Mean Age (years) | 47 |
| Minimum Age (years) | 23 |
| Maximum Age (years) | 81 |
| Glaucoma Patients | 15 |
| Non-Glaucoma Patients | 7 |
| East Asians | 16 |
| Caucasians | 6 |
| Male | 13 |
| Female | 9 |

The data was annotated by tracing out the center of the trabecular meshwork as well as the iris border with curves on all 378 images, and all annotations were subsequently confirmed by two glaucoma specialists.

Neural Network Models

The core element of our approach to identifying the trabecular meshwork is a U-net, which a CNN configured as an encoder and decoder network that is able to generate predictions for every pixel in an image with very high computational efficiency. We trained and used this CNN on RGB video frames that were down-sampled to a size of 512×288 pixels—this reduces the computational cost of generating predictions with the CNN and enables the use of larger CNN models. The neural network was trained to predict not only the TM line itself but also the iris border for each pixel in the image. While predicting the iris border is not of great interest by itself, it has been shown that having ancillary prediction objectives for similar tasks helps the model in learning better features and obtain a higher accuracy on the original task; this process is known as multitask learning. Several models were compared against each other in this study, as follows:

(1) A straight horizontal line fit to the human annotations of training images, used as a simple baseline.

Figure 2:
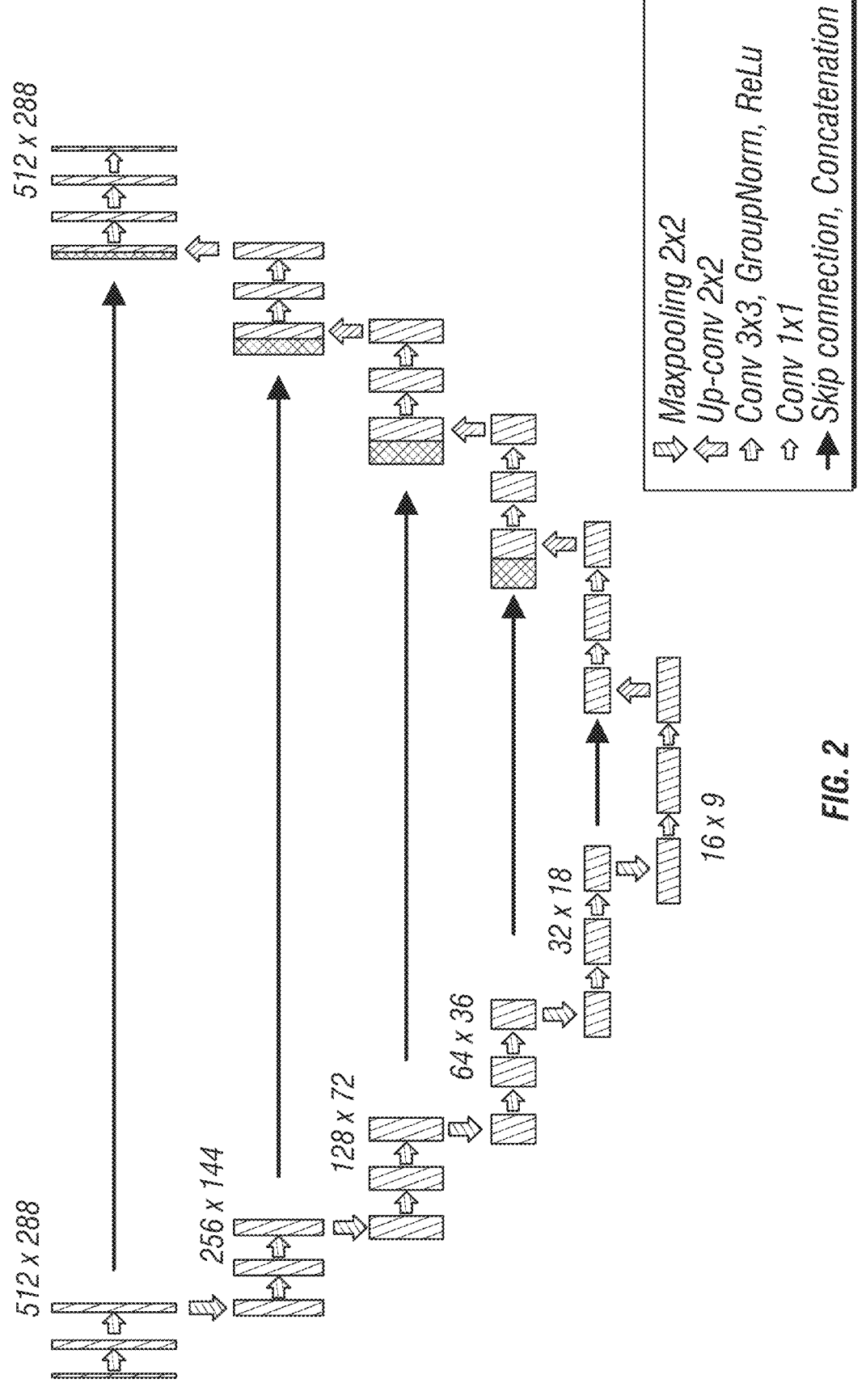
FIG. 2 is a diagram of a base U-net model that was used in a herein-described embodiment of a system and method for identification of the TM within a subject's eye. The input is a 3-channel RGB image resized to 512 by 288 pixels, which is then processed with a series of convolutional layers. The model generated predictions for each pixel, both for the iris border and the position of the TM The contracting and expanding paths of the model are necessary to enable the model to aggregate information from the entire image instead of just small areas. The mode contains a total of 23 convolutional layers, 5 max-pooling layers with 5 corresponding up-sampling operations in the decoder branch. The model has a receptive field of 315 pixels for the deepest layer in the encoder, which is sufficient to cover the re-sample image frame along its height.

(2) A U-net model as shown in the diagram of FIG. 2, using group normalization and the standard weight initialization method of using scaled random values.

(3) A U-net model with a VGG16 encoder model with weights that were pre-trained on the ImageNet data set of 1.2 million natural images, and subsequently optimized on our gonioscopy data set. While ImageNet contains virtually no medical images, It has been shown that transfer learning generally benefits the model's accuracy. The model is similar to the one depicted in FIG. 2 but contains additional convolutional layers in the encoding network and no group normalization layers.

(4) A U-net model with a VGG16+BN encoder, which uses batch normalization layers after each convolutional layer but is otherwise identical to (3) and also pre-trained on ImageNet.

(5) Two other model variations were tested in preliminary experiments but were found to not perform statistically significantly better—these models and results were described in the Supplementary Material.

CNN Training Targets for Accurate Line Predictions

There are several ways of applying deep learning to the problem of identifying structures such as the trabecular meshwork in images. The most commonly used and direct way would be to use a pixel-wise segmentation model, such as a U-net, and predict each pixel that is close to the TM as 1 and everything else as 0. While this is the standard approach in image segmentation [28], the potential disadvantages are that the user must specify a somewhat arbitrary thickness of the TM line beforehand, and model accuracy and training behavior would depend on this factor, and predictions are sensitive to threshold selection. Alternatively, this problem could be avoided by predicting the curve that marks the center of the TM directly, either by predicting polynomial factors, or segments of a spline graph. However, this second approach can be sensitive to artifacts in any part of a video frame, which could cause the entire frame's prediction to be incorrectly shifted without any recourse to automatic fault detection and correction techniques that could be applied in the first approach.

Figure 3:
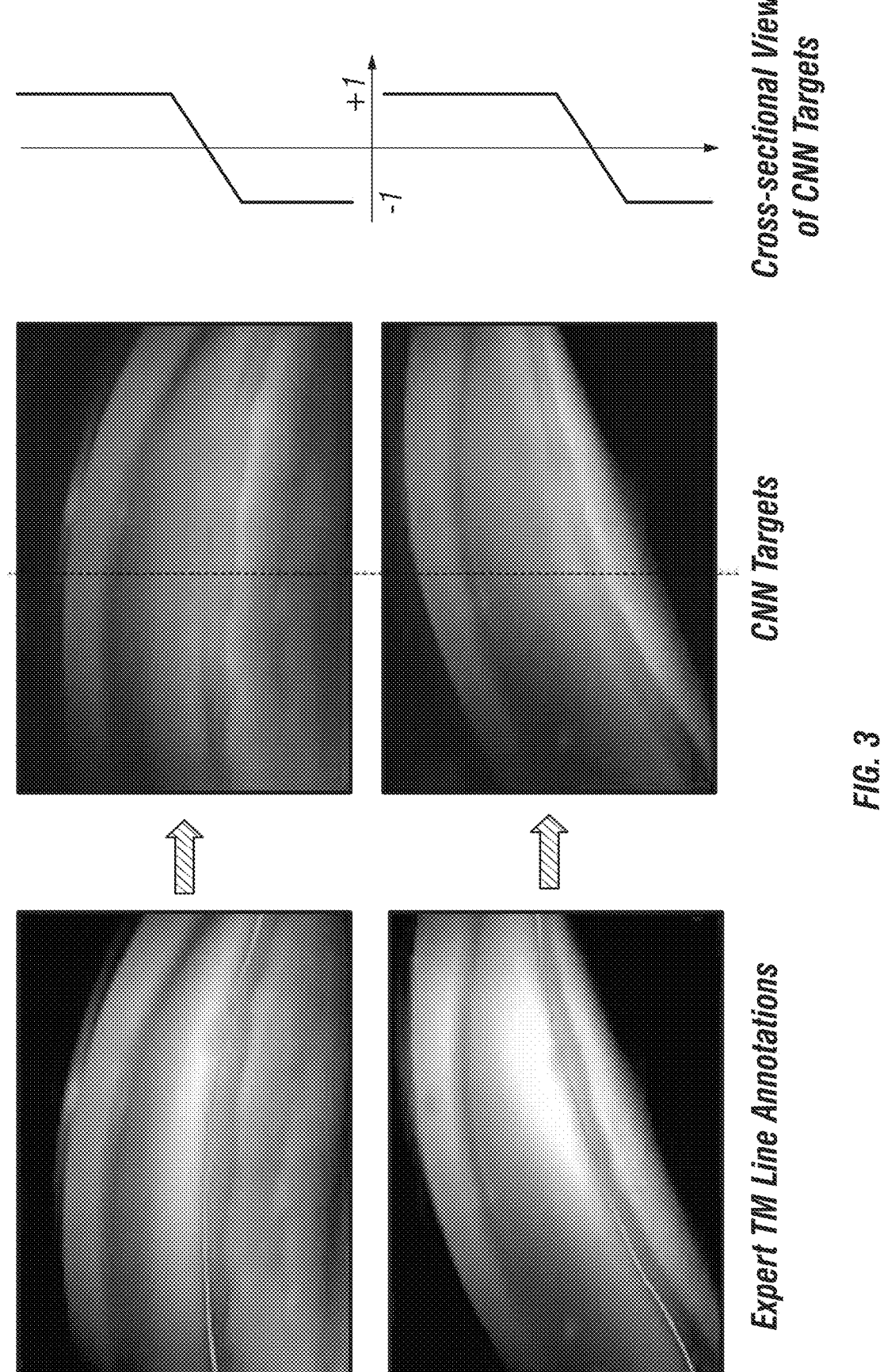
FIG. 3 shown an exemplary visualization of the CNN training targets for the vertical direction (center image, red values indicate a positive offset while blue indicate negative target values) overlaid on the original images. The human expert annotations (green lines in the images on the left) were converted into per-pixel targets with values indicating the distance and direction towards the TM line along the vertical axis (top/down), capped at ±30 pixels, and then normalized to the range of −1 to 1 to facilitate training. Of note, the red dot in the image was the focusing beam for the selective laser trabeculoplasty (SLT) as this image was taken from the video frame of a patient undergoing SLT.
Figure 4:
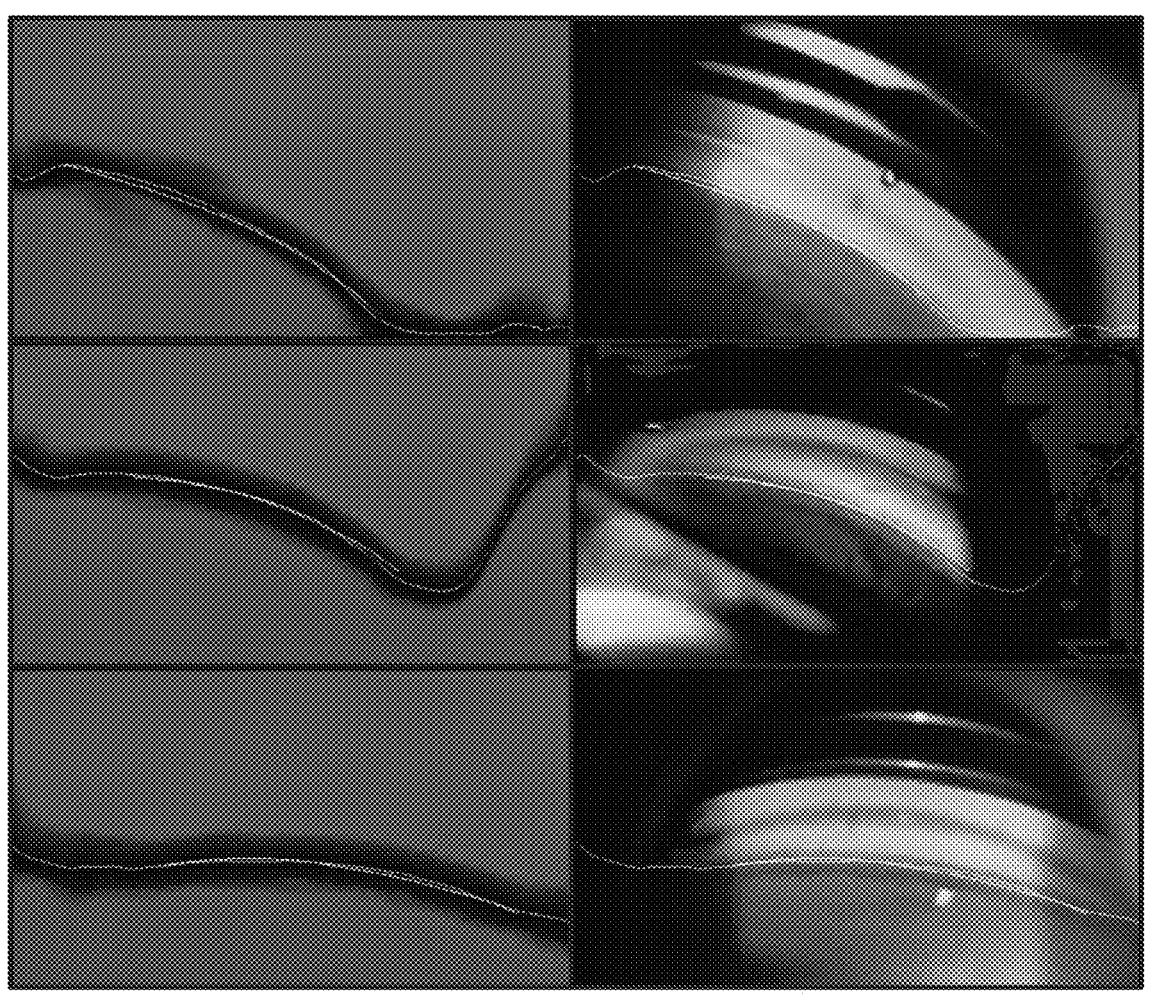
FIG. 4 shows offset predictions (images on the left) for the TM line by the VGG16 U-net model for test set images, along with the predictions overlaid on the original images (on the right). The offsets are color and intensity-coded in red/blue for positive/negative values. Also indicated are the human annotations as white curves, and the final curve predictions of the model in green, computed from the predicted offsets using the post-processing procedure described herein.

A combination of both approaches was chosen, where the model predicts, for each pixel in the image, what this pixel's distance is to the center of the human annotation of the TM's center, as well the direction towards the TM, encoded as positive or negative values. The distance targets were then capped to ±30 pixels (which amounts to ±10% of the re-scaled image's height) and then normalized to the range of −1 to 1 as shown in FIG. 3 to facilitate training. Without capped targets, the model would be forced to spend disproportionately much effort on points far from the TM line, due to the quadratic scaling when using the mean-squared error loss function for training. To further ensure that the model's distance predictions close to the TM line were accurate, a pixel-mask was used to up-weight the loss function by a factor of 5 for all points within 30 pixels of the TM/iris line. Regions where the TM line was not clearly visible were not labeled and a mask was used to set the training loss to zero along the corresponding pixel columns, thus excluding the regions from affecting the training process in any way.

Data Augmentation and Normalization

Data augmentation was used to increase the expected generalization performance and accuracy of machine learning models on future test cases by applying small random transformations to the training data during the training process. This prevents the model from becoming overly specialized to minor details that might be present in the training data, and more robust to variations in appearance, such as the exact color of the iris, illumination, or position and orientation of the TM within the image. The following types of data augmentation were used: horizontal mirroring, random translations of images up to ±10% of the image height, rotations up to ±25 degrees, shearing up to ±20 degrees, zooming up to ±10% of the image height, and small random changes to the color balance of the red/green/blue channels of an image (this makes the image deviate from the default white balance). Any pixels with missing values after augmentation (such as after translating, shearing, or rotating the image) were populated by replicating the closest pixel values of the image.

The data augmentation was applied to generate new training samples live during training the CNN models, while mirroring the same augmentations of the data to the training targets of the CNN. Before being used as an input to the CNN, each augmented video frame was normalized to a pixel value with a range of 0 to 1. We further applied white-balancing to the frames, equalizing the mean pixel-values of the R, G, and B channels on a frame-by-frame basis, followed by normalizing the luminosity of each frame. However, as some frames were only partly illuminated, this step would cause them to be partly over-saturated—to prevent this, only pixels with a mean luminosity 0.25 (after 0-1 scaling) were considered for the luminosity normalization of each frame.

Cross-Validation Study and Training

The neural networks were trained in a per-patient stratified ten-fold cross-validation. In each cross-validation fold all annotated frames from two or three different patients were reserved for testing (as we have images from 25 patients for training in total). The annotated frames from the remaining patients were used for training the neural network (85% of these images) or for validation (the remaining 15%). The distribution of images into training and validation subsets was randomized. The validation set was used for monitoring the training progress, hyperparameter optimization, and selecting the best model for final evaluation on the test set (thus avoiding selecting a model based on test error). This cross-validation experiment consisted of ten repetitions/folds, such that each patient's frames were used as a test case exactly once. The main benefit of this approach was the lower variance in estimating the neural network's generalization accuracy than what would be achievable with a single train/validation/test split. It further avoided the problem of correlated training and test sets as frames from one patient were never part of both the training and test set.

The loss function for gradient-based training was a pixel-wise-weighted and mean-squared error function. All predictions within 30 pixels of the ground truth annotation line were weighted higher by a factor of 5 compared to pixels farther away. The training targets were capped vertical offsets of each pixel to the annotations, as described in more detail in Section 2.3. In addition to the pixel-wise loss, an auxiliary loss was used which was based on the model's post-processed TM line predictions for the training examples (as described in Section 2.6 below, but without additional filtering rounds) and the mean-squared error loss was used to score the distance between the predicted curve and the human annotations along the vertical axis of the image.

All neural networks were trained with the Adam optimizer for approximately 250 epochs (determined by hyperparameter optimization as described in Section 2.5). The learning rate was slowly ramped up during the first five epochs of training ("warm-up phase" [30]) and then trained at a learning rate that was gradually reduced by a factor of 100 to 1000 over the course of training. Early stopping was used to reduce overfitting, by monitoring the model's curve predictions (after post-processing) on the validation set after each epoch.

Hyperparameter Optimization

Hyperparameter optimization was used to find the best configuration of parameters that specify the training process and neural network architecture. A hill-climbing random search protocol was used to perform the optimization, as it performed reasonably well in high-dimensional search spaces with noisy validation scores. Some of the parameters that were optimized were: the initial learning rate, learning rate decay rate, number of training epochs, batch size, number of convolutional filters per layer (except for VGG16-based networks), number of group normalization channels, and loss mask scaling far from the line.

The hyperparameter optimization was performed using the validation score for each of the ten cross-validation splits separately, to avoid cross-optimizing on the test set. For each optimization run a total of 10 models were trained and evaluated, thus resulting in a total of 100 trained models for each cross-validation experiment. For each cross-validation split, the model with the best validation score was chosen to be used as final exemplar for testing on the uncorrelated test split. Similarly, to form ensembles of models, the best 5 models were chosen, and their predictions were averaged.

To compute the final test scores, the best model of each cross-validation fold was selected among the 10 trained models, judged based on their accuracy on the respective validation set (not the test set). The ten resulting top cross-validation models were then used to predict the position of the TM on their respective (non-overlapping) test sets, yielding a total of 378 test predictions.

Postprocessing of Predictions

The model predictions were converted into a single curve in a computationally efficient way to allow real-time use. By design the model predicted offsets to the TM line (and iris border) for every pixel in the image, capped at ±30 pixels (see FIG. 3). Predictions with an absolute value above 70% of this cap (i.e. >±21 pixels) were discarded and the remaining offset predictions were averaged, resulting in a single height prediction. This could be done computationally more efficiently by pixel-wise addition of a pre-computed offset mask to the predicted (non-discarded) offsets and simply averaging the results per pixel column in the image. The offset mask consisted of the numbers from 1 up to the image height in pixels (288) in increments of 1. A major strength of this approach was that the final predicted curve positions were effectively made by a committee with approximately 43 votes per column, which resulted in a globally contiguous curve without requiring additional smoothing or costly interpolation functions. However, the procedure described above was still sensitive to incorrect outlier predictions even if they were far from the predicted curve. To address this, the averaging process over all non-discarded predicted offsets was repeated three times, with each time only averaging offset predictions up to X pixels away from the last iteration's predicted curve, where X took on the values: 84, 42, and 21. This ensured that the final predicted curve only depended on local offset predictions and ignored potential incorrect predictions or artifacts in other locations in the image.

FIG. 3 shows a comparison of offset predictions for the TM line by the VGG16 U-net model for test set images (on the left) with the predictions overlaid on the original images (on the right). The offsets are color-coded and intensity-coded in red/blue for positive/negative values. Also indicated are the human annotations as white curves, and the final curve, predictions of the model in green, computed from the predicted offsets using the post-processing procedure described above.

Performance Comparison: CNN Model Vs Ophthalmologists

Fifteen gonioscopic images were selected from publicly available sources as well as some a teaching collection maintained by an experienced glaucoma surgeon (none of which were duplicative of images used as training or validation sets for our CNN model). These images were chosen to represent varying levels of difficulty for one to identify the TM. Ground truth was established by agreement among three experienced glaucoma surgeons.

In order for the model to score correctly on a given question, the entirety of its predicted trabecular-meshwork line needed to correspond to the ground truth. To facilitate reaching a larger group of ophthalmologists, we converted the TM identification task into a multiple-choice question, with each gonioscopic image showing four letters corresponding to different angle landmarks. Each participant was asked to pick the letter corresponding to the TM. This multiple-choice test, which we called "Gonio Challenge," was hosted as a survey on REDCap (Vanderbilt University, Nashville, TN) and could be accessed at https://lin.hs.uci.edu/AIG. A total of 25 comprehensive and cornea specialists, 10 glaucoma specialists, and 25 ophthalmology residents and fellows participated in this survey.

Survey results were exported directly from REDCap to Microsoft Excel. The average±standard deviation for each of the three groups of ophthalmologists were recorded. The CNN model performance was compared to each of the three groups of ophthalmologists by determining the z score, wherein a z score>2 indicated that the model scored greater than 97 percentile of the group of ophthalmologists being compared.

Statistical comparison among the three surveyed ophthalmologist groups were performed using a two-tailed, equal-variance t-test, with p<0.05 indicating statistical significance.

Figure 5:
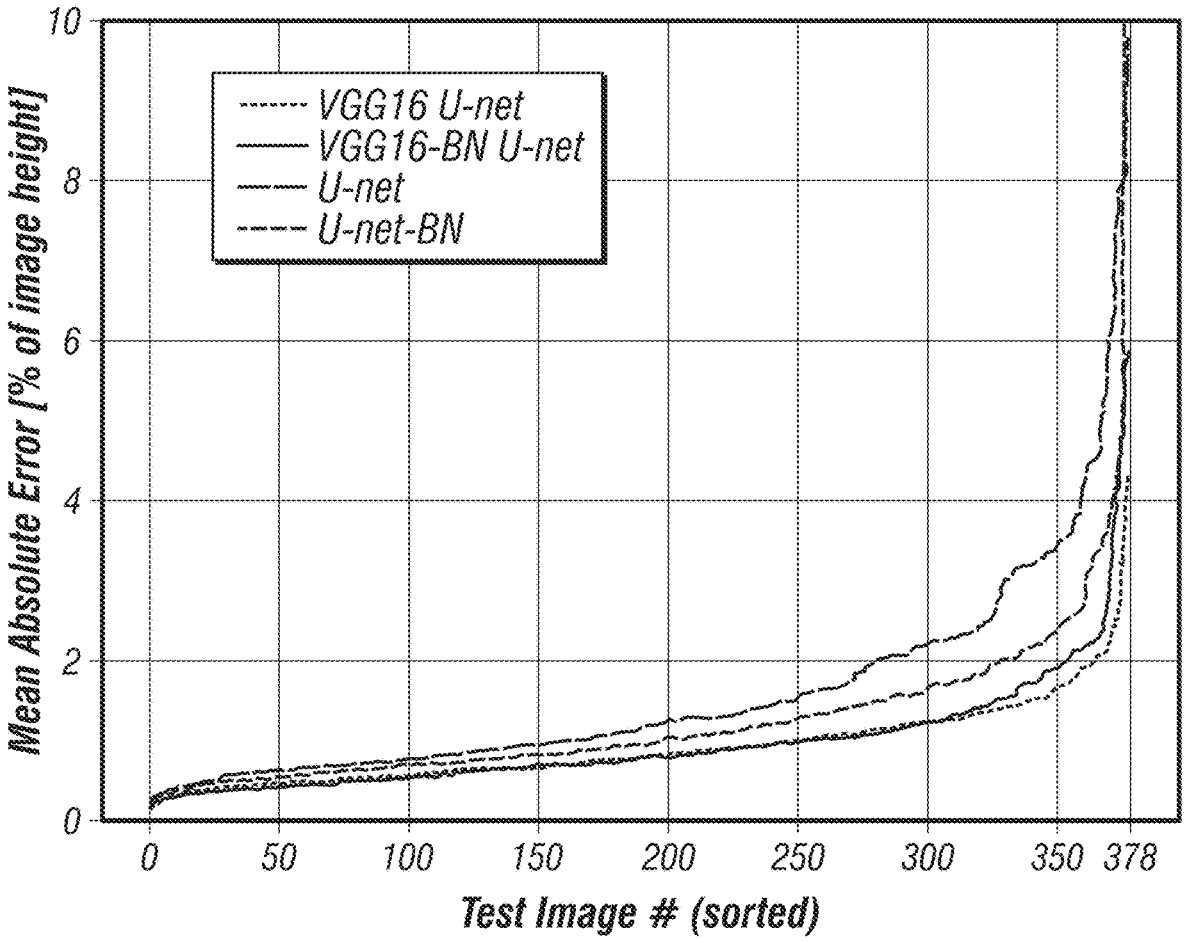
FIG. 5 is a graph showing average absolute error of predicted TM lines compared to human annotations for three different CNN architectures on test frames. Shown is the per-image average error of the predicted TM lines for each of the 378 cross-validation test split images. Error scores in this graph are sorted low-to-high for clarity.

Results:

For each CNN architecture, its combined 378 test set predictions were cored against the human annotations by computing the absolute distance along the vertical axis between the predicted and the annotated curves for each pixel column, ignoring predictions in columns for which no annotation was present, due to the TM line being off-frame or not visible for different reasons. The individual errors were then averaged per image to ensure that the varying line length of the TM annotations does not influence the final results, which could otherwise be biased towards easier targets where long sections of the TM are clearly visible. FIG. 5 graphically shows the average prediction for each of the 378 test images for four different CNN architectures that were evaluated.

Model Performance and Validation

Tables 2 and 3, below, show the average and the median of all test and validation scores for three CNN architectures, as well as for ensembles of these models.

TABLE 2

| | Test Set Errors | | | |
| --- | --- | --- | --- | --- |
| Model | 1 model [mean] | Ensemble [mean] | 1 model [median] | Ensemble median] |
| Baseline [line] | 13.4 ± 0.3 | — | 12.4 ± 0.3 | — |
| VGG16 U-net | 0.64 ± 0.02 | 0.63 ± 0.02 | 0.56 ± 0.01 | 0.53 ± 0.02 |
| VGG16 U-net* | 0.76 ± 0.03 | 0.71 ± 0.02 | 0.61 ± 0.02 | 0.58 ± 0.02 |
| VGG16-BN U-net | 0.64 ± 0.02 | 0.66 ± 0.02 | 0.55 ± 0.01 | 0.56 ± 0.01 |
| U-net | 1.06 ± 0.04 | 1.57 ± 0.09 | 0.93 ± 0.03 | 1.05 ± 0.04 |
| U-net-BN | 0.77 ± 0.03 | 0.75 ± 0.03 | 0.62 ± 0.02 | 0.62 ± 0.02 |

Table 2 shows cross-validation test set errors, measured as a percentage of the image height, of TM line predictions by neural networks when compared against human expert annotations. The vertical absolute errors of the predicted curve compared to the annotations are averaged per image, and the values shown in the tables are the median and average of the per test image errors. The standard error of the mean is shown for the average scores, and analogously the median absolute deviation is displayed for the median scores. Ensembles are created by averaging the predictions of the 5 best models, ranked by validation set scores. (*trained to predict distances within ±60 px instead of the default of ±30 px).

TABLE 3

| | Validation Set Errors | | | |
| --- | --- | --- | --- | --- |
| Model | 1 model [mean] | Ensemble [mean] | 1 model [mean] | Ensemble [mean] |
| Baseline [line] | 13.4 ± 0.3 | — | 12.4 ± 0.3 | — |
| VGG16 U-net | 0.64 ± 0.02 | 0.63 ± 0.02 | 0.56 ± 0.01 | 0.53 ± 0.02 |
| VGG16 U-net* | 0.76 ± 0.03 | 0.71 ± 0.02 | 0.61 ± 0.02 | 0.58 ± 0.02 |
| VGG16-BN U-net | 0.64 ± 0.02 | 0.66 ± 0.02 | 0.55 ± 0.01 | 0.56 ± 0.01 |
| U-net | 1.06 ± 0.04 | 1.57 ± 0.09 | 0.93 ± 0.03 | 1.05 ± 0.04 |
| U-net-BN | 0.77 ± 0.03 | 0.75 ± 0.03 | 0.62 ± 0.02 | 0.62 ± 0.02 |

Table 3 shows cross-validation validation set errors, measured as a percentage of the image height, of TM line predictions by neural networks when compared against human expert annotations. The vertical absolute errors of the predicted curve compared to the annotations are averaged per image, and the values shown in the tables are the median and average of the per test image errors. The standard error of the mean is shown for the average scores, and analogously the median absolute deviation is displayed for the median scores. Ensembles are created by averaging the predictions of the 5 best models, ranked by validation set scores. These validation set results are expected to be better than the test set errors shown in Table 2 due to selection bias and correlation between training and validation set. (*trained to predict distances within ±60 px instead of the default of ±30 px).

The test set predictions of the best CNN (VGG16 U-net without batch normalization) has a median deviation of merely 0.8% of the frame height compared to human annotations. This error is significantly lower than the typical width of the TM line, which shows that the models reliably learned to predict the center of the TM. As shown graphically in FIG. 5, even the worst test frame prediction of this CNN has an average error of around 4% of the frame height, which is effectively still a usable prediction of the TM's position. The other two CNN models fail to accurately predict the TM's position to within 5% of the image's height in 2-10 out of the 378 test cases, while succeeding on the remaining 97.4% test frames. The very simple baseline of fitting a horizontal line through the training and validation images shows that the CNN predictions are more than one order of magnitude more accurate in all cases and metrics. We also observed that the non-VGG CNNs had problems converging during training when not using batch/group normalization ("-BN" in Tables 1 and 2), whereas the pretrained (VGG) CNNs did not benefit from batch normalization in any significant way. We further investigated if the models are sensitive to the choice of training them to predict the distance to the curves only within a band of ±30 pixels, by also training the same CNN to predict distances within ±60 px of the curve ("VGG16 U-net*" in Table 1), but found them to be equivalent within statistical variation.

CNN Model Labeling Trabecular Meshwork in Intraoperative Videos

Figure 6:
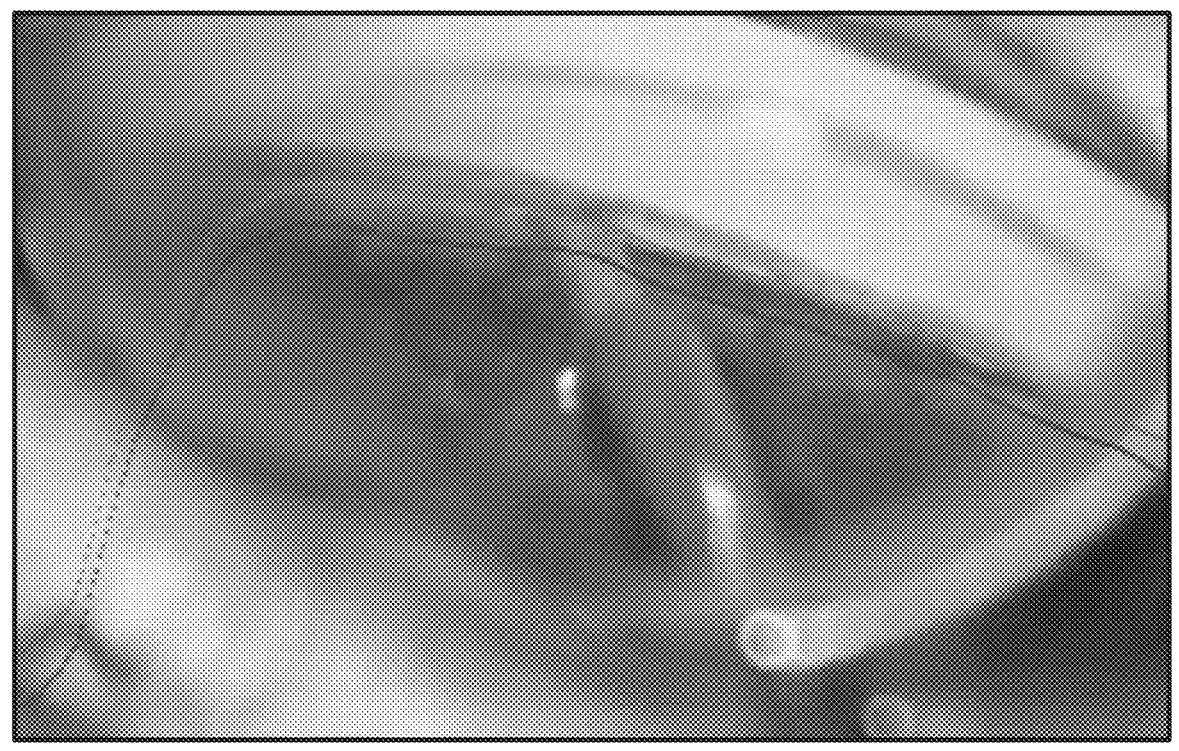
FIG. 6 is an exemplary test video frame showing identification of the TM during an ab interno trabeculotomy procedure performed with the Trabectome® system (Micro-Surgical Technology, Redmond, WA). The green line denotes the CNN model's prediction of the meshwork and the red line marks the iris border. The CNN model's accuracy was unaffected by the presence of the Trabectome handpiece. Artifacts could be seen near the edge as one moved beyond the gonioprism's field of view.
Figure 7:
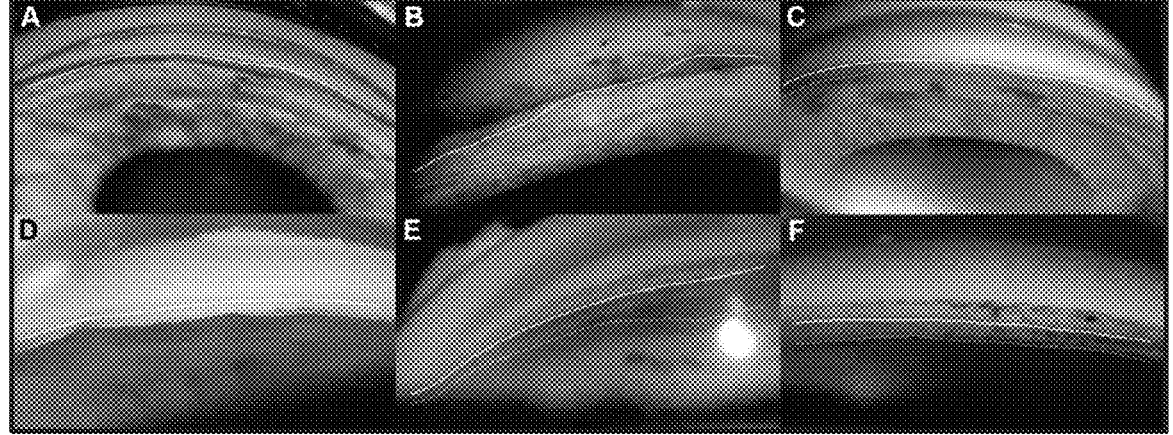
FIG. 7 is a composite of gonioscopic image displays with CNN Model predictions of trabecular meshwork position, with the green line indicating the TM and the red line indicating the iris border. In frames A and B, the model correctly identified the TM on the right side of the image but failed to trace it toward the center and left side of the images. In frames C through F the TM and iris boarder are correctly labeled by the CNN model.

The model was able to correctly outline the trabecular meshwork in intraoperative videos obtained with different gonioprisms, magnifications, cameras, contrast, lighting, hue and saturation. In all three videos of ab interno trabeculotomy with the Trabectome, the model identified the trabecular meshwork, even in the presence of the Trabectome handpiece, which could be seen essentially tracing the path outlined by the model. The model would have no knowledge of the fact that the handpiece was traveling along the path that marked the trabecular meshwork as the model itself was trained in the absence of any surgical instrument present in the angle. FIG. 6 shows an exemplary frame of identification of the trabecular meshwork during ab interno trabeculotomy with Trabectome in a test video. The green line shown on FIG. 6 denotes the CNN model' prediction of the meshwork and the red line marks the iris border. The CNN model's accuracy was unaffected by the presence of the Trabectome handpiece. Artifacts could be seen near the edge as one moved beyond the gonioprism's field of view. Gonioscopy Challenge: CNN Model Vs. Ophthalmologists FIG. 6 shows a comparative compilation of gonioscopic images (Images A through F) on which the CNN Model prediction is displayed by a green line indicating the TM and the red line indicating the iris border. In Frames A and B the model correctly identified the TM on the right side of the image but failed to trace it toward the center and left side of the images. Frames C through F are examples of images wherein the CNN Model correctly labeled the TM and iris border.

There were no incomplete responses in our survey from human participants. The three glaucoma experts reached consensus on all fifteen questions. The CNN model missed two of the fifteen questions in the gonioscopy challenge. In both questions, the model correctly labeled the trabecular meshwork toward the right corner of the image but mis-identified at the center and left side of the images (FIGS. 6A and 6B). Several other correctly labeled images by the CNN model were shown in FIG. 6C-F. In other words, the model scored 86.7% (13 out of 15). This performance was comparable to the aggregate group performance of the glaucoma specialists (85.3%±5.3%, z=0.253, 60th percentile). The CNN model scored significantly better than residents and fellows (74.7%±10.9%, z=1.1, 86th percentile), as well as cornea and general ophthalmologists (72.8%±6.6%, z=2.09, 98.1th percentile). In other words, the model performed more than two standard deviations above the mean of the surveyed cornea and general ophthalmologists, and one standard deviation above the mean of the residents and fellows.

Glaucoma specialists also performed significantly better than the cornea and comprehensive ophthalmologists as well as the resident and fellows (p<0.05 in both groups). There was no statistical difference between the cornea and comprehensive ophthalmologist group versus the resident and fellows group (p=0.467).

Discussion

The salient findings and contribution of the study were 1) deep learning models could be trained with a relatively small dataset to accurately identify trabecular meshwork in gonioscopy, 2) our CNN model was computationally efficient and could be applied in real time, 3) our CNN model performed well even in intraoperative videos that appeared significantly different from their training data which were all still gonioscopy photos, 4) our CNN model performed similarly to glaucoma specialists, but outperformed the majority of ophthalmology residents, fellows, cornea specialists and comprehensive ophthalmologists, and 5) our data set is the first publicly available labeled gonioscopy image dataset.

The above described study demonstrated how deep learning can be used to locate and mark the location of the trabecular meshwork under gonioscopic view in real-time and with very high accuracy. The best-performing model predicts the location of the TM correctly (<5% average error relative to the frame height) for all of the 378 test frames, and with an average error of only 0.9% of the frame height compared to human expert annotations. This CNN model was based on pre-trained weights from a VGG16 model that was pre-trained on the ImageNet data set, which contains a large number of non-medical natural images and was then re-trained as part of a larger U-net model on our gonioscopic data set. The observation of achieving significant gains in model accuracy by using this transfer learning process has been made in the context of many prior medical image analysis problems that used deep learning in the past. It can be interpreted as being equivalent to obtaining additional training data, which always increases model accuracy.

Each individual CNN model trained in this study can run in real time applications, achieving a single-frame operation throughput of at least 35 frames per second on a modern GPU (for the VGG16 based U-net on a Pascal Titan X). While this is not the case with ensembles of these models (which tend to offer a very slight accuracy improvement), a significant amount of research exists on compressing and accelerating groups or individual models, which allows trained neural networks to be converted into faster networks while preserving their predictive accuracy.

One common pitfall of deep learning is a degraded accuracy when the test population differs significantly from the training population [33]. Our CNN model, however, showed remarkable accuracy on intraoperative videos from other surgeons. Intraoperative gonioscopy procedures have magnification, field-of-view, aspect-ratios, hue, contrast, image composition, and lighting that were all significantly different from the slit-lamp gonioscopy photos. We believe that our model's ability to adapt to different testing sets is in part due to the model's inherently robust design. Our CNN model combines the strengths of a pixel-wise segmentation algorithm (such as the U-Net) as well as a curve-predicting algorithm that best-fits the trabecular meshwork. Our model would generate a vector map at each pixel that denoted how far and where that pixel was from the trabecular meshwork and an overall decision was then made by the CNN model based on the area averaging of the vector map. The data augmentation and hyperparameter optimization in our model also helped to mitigate prediction errors from changes in lighting, magnification and image composition. As such, even in the presence of a surgical instrument, such as a Trabectome handpiece, the model was able to predict the location of trabecular meshwork.

Furthermore, our CNN model performed on par with glaucoma specialists; the model placed at 60 percentile when compared to this group, and at 98 percentile when compared to general ophthalmologists and cornea specialists. It is important to note that our survey design would give our CNN model a slight disadvantage. Unlike human ophthalmologists, the model was asked to delineate the entire length of the trabecular meshwork instead of simply choosing a letter that best describes the meshwork location. In other words, if any portion of the model's predicted meshwork line fell outside of the actual TM, that question was marked as incorrect. This was in fact what happened to both of the questions that our CNN model missed in the survey. In both questions, the model correctly labeled the meshwork toward the right side of the image but missed the target at the center and left side of the image. One likely explanation for the model's mistakes was that one image was significantly more minified (FIG. 7, Frame A) than the images the model encountered during training; nearly the entire pupil margin could be seen in FIG. 7, Frame A. Furthermore, in both images, the iris color was very similar to the cornea reflection (FIG. 7, Frames A and B) and also very dissimilar from the iris color in the training images, which caused the iris border to be incorrectly segmented in both cases as well.

These mistakes would very likely be resolved with greater numbers and heterogeneity in the training data. Our dataset was the major limitation in this study. The dataset contained only patients with open angle and no angle pathologies or prior angle surgeries. Although the dataset had a relatively normal distribution of angle pigmentation, it was obtained from only East Asians and Caucasians. Future studies and collaborations will be needed to expand on our current dataset and the authors have made the dataset with annotations public to encourage this effort. Nonetheless, it was remarkable that with a relatively small dataset, our CNN model was able to accurately identify the trabecular meshwork.

Proper identification of iridocorneal structures on gonioscopy in a clinical setting is a difficult skill, yet crucial for diagnostic and therapeutic purposes. The pigmentation and appearance of these structures may vary widely between individuals. The trabecular meshwork is the target of laser trabeculoplasties as well as most forms of MIGS. In the last decade there has been an increase in gonioscopy-based surgeries performed by both general ophthalmologists and glaucoma specialists. In our survey, we found that glaucoma specialists performed significantly better at identifying the trabecular meshwork than general ophthalmologists and cornea specialists. Altogether, these observations highlight the importance that surgeons must be able to properly identify these highly varied structures in clinical practice. While techniques such as indentation and the corneal wedge are powerful adjuncts to gonioscopy at the slit lamp, they are mostly not applicable during gonioscopy-based intraoperative procedures. Our proposed neural network model could accurately identify the TM in both slit-lamp and intraoperative gonioscopy, and potentially serves an adjunctive role augmenting diagnostic accuracy and surgical safety.

The neural network model described herein can have applications in surgical training, automated screenings, and intraoperative guidance. As the model is deployed, significantly more and diverse training data could be obtained, thus creating a positive feed-back loop to further improve model accuracy and generalization capabilities. In turn, this would increase the model's applicability, in particular in critical settings, such as providing real-time guidance during surgeries.

As described above, in some embodiments, data augmentation may be used to increase the expected CNN performance and accuracy of machine learning models on future test cases by applying small random transformations to the training data during the training process.

Also, as described above, in some embodiments cross-validation may be performed during training of the neural networks.

Also, as described above, in some embodiments hyper-parameter optimization may be used to find the best configuration of parameters that specify the training process and neural network architecture.

Also, as described above, in some embodiments model predictions may be subjected to post-processing to clarify the marking (e.g., delineation, accentuation, darkening, coloring, annotation, labeling, indication with an arrow or pointer, or other identification).

The systems and methods described herein may be integrated in surgical microscopes, surgical robots, automated ophthalmic screening devices, etc. and may be used in various applications such as surgical training, automated screenings, and intraoperative guidance.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, he articles "a" and "an" are used herein to refer to one or to more than one (i.e., to at least one) of the grammatical object of the article. By way of example, "an element" means one element or more than one element.

Although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for identifying an anatomical structure or tissue type within an eye of a subject, said system comprising:

a viewing device for viewing an area within the eye which includes the anatomical structure or tissue type;

a camera or imaging device;

an image processor; and a display device;

wherein the camera or imaging device acquires an image of the area viewed by the viewing device;

wherein the image processor uses deep learning to identify the anatomical structure or tissue type on said image; and wherein the display device displays an enhanced image on which the anatomical structure or tissue type is marked;

wherein the image processor comprises a non-transitory data storage medium having recorded thereon a deep-learning generative model that outputs said enhanced image on which the anatomical structure or tissue type is marked;

wherein the deep-learning generative model comprises at least one Convolutional Neural Network (CNN) that has been trained using data augmentation; and wherein any pixels with missing values after augmentation were populated by replicating the closest pixel values of the image.

2. A system according to claim 1 wherein the viewing device is selected from: goniolens, gonioprism, gonioscope, retnascope, ophthalmoscope and surgical microscope.

3. A system according to claim 1 wherein the camera or imaging device comprises a still camera or a video camera.

4. A system according to claim 1 wherein the image processor comprises a computer or processor.

5. A system according to claim 1 wherein the display device is selected from: a video screen, monocular or binocular eyepiece, virtual reality headset/goggles/glasses.

6. A system according to claim 1 wherein the anatomical structure or tissue type is selected from: trabecular meshwork, macula, retinal pigment epithelium, optic nerve head, epiretinal membranes.

7. A system according to claim 1 wherein the viewing device views the iridocorneal angle and the anatomical structure or tissue type is trabecular meshwork.

8. A system according to claim 1 wherein the anatomical structure or tissue type is marked on the enhanced image by a type of marking selected from: delineation, accentuation, darkening, coloring, annotation or indication with an arrow or pointer.

9. A system according to claim 1 wherein;

said at least one Convolutional Neural Network (CNN) comprises a plurality of Neural Encoder-Decoder Convolutional Neural Networks (U-nets) trained to identify the anatomical structure or tissue type, and the image processor is programmed to apply said Neural Encoder-Decoder Convolutional Neural Networks CNNs-(U-nets).

10. A system according to claim 1 wherein the system is equipped to transmit the enhanced image to a local or remote secondary location.

11. A system according to claim 10 wherein the secondary location is selected from: a local or cloud-based data storage medium, hard drive, intraoperative recording device, remote computer, remote display, telemedicine terminal, medical records database or surgical robot.

12. A system according to claim 1 wherein said at least one Convolutional Neural Network (CNN) is configured as an encoder and decoder network that is able to generate predictions for every pixel in said image.

13. A system according to claim 12 wherein said at least one Convolutional Neural Network (CNN) is trained using video image frames that are down-sampled to a size of 512×288 pixels.

14. A system according to claim 13 wherein said at least one Convolutional Neural Network (CNN) is trained by a method which uses multitask learning, whereby said at least one Convolutional Neural Network the (CNN) is trained to predict not only the target anatomical structure or tissue type but also an ancillary anatomical structure or tissue type.

15. A system according to claim 14 wherein:

the target anatomical structure or tissue type is trabecular meshwork; and the ancillary anatomical structure or tissue type is iris border.

16. A system according to claim 1 wherein the data augmentation comprises at least one of:

horizontal mirroring;

random translations of images up to ±10% of the image height;

rotations up to ±25 degrees;

shearing up to ±20 degrees;

zooming up to ±10% of the image height; and small random changes to the color balance of any red/green/blue channels of an image.

17. A system for identifying an anatomical structure or tissue type within an eye of a subject, said system comprising:

a viewing device for viewing an area within the eye which includes the anatomical structure or tissue type;

a camera or imaging device;

an image processor; and a display device;

wherein the camera or imaging device acquires an image of the area viewed by the viewing device;

wherein the image processor uses deep learning to identify the anatomical structure or tissue type on said image;

wherein the image processor comprises a non-transitory data storage medium having recorded thereon a deep-learning generative model that outputs said enhanced image on which the anatomical structure or tissue type is marked; and wherein the deep-learning generative model comprises one or more Convolutional Neural Networks (CNNs) and the display device displays an enhanced image on which the anatomical structure or tissue type is marked and wherein cross-validation was applied during training of the one or more CNNs.

18. A system according to claim 17 wherein the cross-validation comprises per-patient stratified ten-fold cross-validation.

19. A system according to claim 17 wherein the anatomical structure or tissue type is selected from: trabecular meshwork, macula, retinal pigment epithelium, optic nerve head, epiretinal membranes.

20. A system according to claim 17 wherein the system is equipped to transmit the enhanced image to a local or remote secondary location selected from: a local or cloud-based data storage medium, hard drive, intraoperative recording device, remote computer, remote display, telemedicine terminal, medical records database or surgical robot.

\* \* \* \* \*